US 9,353,419 B2

(12) United States Patent
Porter et al.

(10) Patent No.: US 9,353,419 B2
(45) Date of Patent: May 31, 2016

(54) BIOMARKERS FOR IAP INHIBITOR THERAPY

(71) Applicants: Dale Porter, Cambridge, MA (US); John Scott Cameron, Belmont, MA (US); Caroline Emery, Brighton, MA (US); Douglas Robinson, Cambridge, MA (US); Kavitha Venkatesan, Waltham, MA (US); Li Wang, Quincy, MA (US)

(72) Inventors: Dale Porter, Cambridge, MA (US); John Scott Cameron, Belmont, MA (US); Caroline Emery, Brighton, MA (US); Douglas Robinson, Cambridge, MA (US); Kavitha Venkatesan, Waltham, MA (US); Li Wang, Quincy, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/398,596

(22) PCT Filed: May 3, 2013

(86) PCT No.: PCT/US2013/039362
§ 371 (c)(1),
(2) Date: Nov. 3, 2014

(87) PCT Pub. No.: WO2013/166344
PCT Pub. Date: Nov. 7, 2013

(65) Prior Publication Data
US 2015/0105434 A1   Apr. 16, 2015

Related U.S. Application Data

(60) Provisional application No. 61/642,899, filed on May 4, 2012.

(51) Int. Cl.
*A61K 31/427* (2006.01)
*C12Q 1/68* (2006.01)

(52) U.S. Cl.
CPC ............ *C12Q 1/6886* (2013.01); *A61K 31/427* (2013.01); *C12Q 2600/106* (2013.01); *C12Q 2600/158* (2013.01); *C12Q 2600/16* (2013.01)

(58) Field of Classification Search
CPC ............ C12Q 1/6886; C12Q 2600/106; C12Q 2600/158; C12Q 2600/16; A61K 31/427
See application file for complete search history.

(56) References Cited

FOREIGN PATENT DOCUMENTS

| CN | 101956014 A | 1/2011 |
|---|---|---|
| WO | 2008057172 A2 | 5/2008 |
| WO | 2010086722 A1 | 8/2010 |
| WO | 2011035083 A1 | 3/2011 |

OTHER PUBLICATIONS

Angileri F F et al: "Nuclear factor—[kappa]B activation and differential expression of survivin and Bcl-2 in human grade 2-4 astrocytomas". Cancer May 15, 2008 us. vol. 112. No. 10. May 15, 2008 pp. 2258-2266.
Duprez Linde et al : "Intermediate Domain of Receptor—interacting Protein Kinase 1 (RIPK1) Determines Switch between Necroptosis and RIPK1 Kinase-dependent Apoptos i s", Journal of Biological Chemistry, vol. 287 , No. 18, Apr. 2012 , pp. 14863-14872.
Gordon G J et al: "Inhibitor of apoptosis proteins are regulated by tumour necrosis factor-alpha in malignant pleural mesothelioma", Journal of Pathology, vol. 211 , No . 4. Mar. 2007, pp. 439-446.
Stanculescu Adina et al: "Estrogen Promotes Breast Cancer Cell Survival in an Inhibitor of Apoptosis (IAP)—dependent Manner" . Hormones & Cancer,vol. 1. No. 3, Jun. 2010, pp. 127-135.
Darding M et al: "IAPs: Guardians of RIPK1", Cell Death and Differentiation 2012 Nature Publishing Group GBR. vol. 19, No . 1, Jan. 2012. pp. 58-66.
Yamaguchi Masayoshi et al :Overexpression of RGPR-p117 suppresses apoptotic cell death and its related gene expression in cloned normal rat kidney proximal tubular epithelial NRK52E cells, International Journal of Molecular Medic Ine , vol. 20, No. 4, Oct. 2007, pp. 565-571.
Bertrand Mathieu J M et al: "ciAP1 and ciAP2 facilitate cancer cell survival by funct ioning as E3 ligases that promote RIP1 ubiquitination". Molecular Cell. Cell Press, Ambridge. MA, us. vol. 30, No. 6, Jun. 20, 2008. pp. 689-700.

*Primary Examiner* — Samantha Shterengarts
(74) *Attorney, Agent, or Firm* — Jennifer Chapman (57) ABSTRACT

A method of selecting a subject having cancer for treatment with an IAP inhibitor.

26 Claims, 2 Drawing Sheets

BIOMARKERS FOR IAP INHIBITOR THERAPY

FIELD OF THE INVENTION

The present invention relates to a method of treating cancer.

BACKGROUND OF THE INVENTION

Apoptosis (programmed cell death) is activated by diverse stimuli, including many that are characteristic of malignant cells including cell cycle deregulation, aberrant signal transduction and stress associated with an unfavorable microenvironment. Cancer cells also demonstrate defects in apoptotic pathways that allow them to evade programmed cell death and that create inherent resistance to many chemotherapeutic agents. The Inhibitors of Apoptosis Proteins (IAPs) are a family of eight proteins defined by the presence of a protein domain, the BIR domain, initially identified in a Baculoviral protein that inhibited apoptosis. Some IAP family members are clearly involved in suppression of apoptosis. The evidence is strongest for XIAP, CIAP1 and CIAP2 (Hunter Apoptosis; 12:1543-1568, 2007), although the mechanisms through which these proteins influence apoptosis are different. There is strong evidence that XIAP directly binds caspases 3, 7 and 9, and that this binding suppresses apoptosis (Deveraux, et al Nature; 388:300-4, 1997). By contrast, the evidence for the CIAP proteins as direct suppressors of caspase activity is weaker. However, the CIAP1 and CIAP2 proteins are components of death receptor signaling complexes where they influence cell survival or death through the Nuclear Factor kappa B (NF-κB) pathway. Activation of death receptor signaling can induce NF-κB survival signaling or apoptosis, depending on cellular context. In some tumor cells, IAP antagonists induce apoptosis via a mechanism that requires TNF-α and RIPK1 (Gaither Cancer Research; 67: 11493-98, 2007). Therefore, IAPs appear to be attractive targets in cancer.

SUMMARY OF THE INVENTION

The present invention is based on the finding that particular biomarkers can be used to select individuals having cancer who are likely to respond to treatment with an IAP inhibitor. Specifically, it was found the level of expression of at least three biomarkers selected from the following group: CXLC10, CCL5, NFKBIA, HERC5, CDYL, STK39, MAPK14, TNF and RIPK1, e.g., the mRNA expression of the biomarkers, can be used to predict whether that individual will respond to treatment with an IAP inhibitor.

In one aspect the invention includes a method of analyzing a biological sample of a subject with cancer including determining a level of mRNA expression of TNF and RIPK1 and one or more (e.g., 2, 3, 4, 5, 6 or 7) of the following biomarkers CXLC10, CCL5, NFKBIA, HERC5, CDYL, STK39 and MAPK14 in the biological sample taken from the subject, wherein the level of expression of the biomarkers in comparison to a control provide an indicator of whether the subject has an increased likelihood of response to an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

In another aspect, the invention includes a method of selecting a subject having cancer for treatment with an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide. The method includes determining a level of mRNA expression of TNF, RIPK1 and STK39 in the biological sample taken from the subject, thereby to predict an increased likelihood of response to an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

In yet another aspect, the invention includes a method of selectively treating a subject having cancer including
a) assaying a biological sample from the subject for a level of expression of TNF and RIPK1 and one or more (e.g., 2, 3, 4, 5, 6 or 7) of the following biomarkers CXLC10, CCL5, NFKBIA, HERC5, CDYL, STK39 and MAPK14 in the biological sample taken from the subject; and
b) selectively administering an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide to the subject on the basis that the sample has a level of expression indicative that the subject has an increased likelihood of response to an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

In still yet another aspect, the invention includes a method of selectively treating a subject having cancer with an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide including administering an TAP inhibitor such as (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide inhibitor to the subject as a result of the subject having an increased level of expression of TNF and RIPK1 and a decreased level of expression of STK39.

The cancer can be any cancer including breast, ovarian, and lung.

The mRNA expression level can be determined in the methods of the invention using RT-PCR.

In another aspect, the invention includes a kit including a plurality of agents for determining the level of mRNA expression of TNF and RIPK1 and one or more (e.g., 2, 3, 4, 5, 6 or 7) of the following biomarkers CXLC10, CCL5, NFKBIA, HERC5, CDYL, STK39 and MAPK14 in a biological sample and instructions for use.

A "biomarker" is a molecule useful as an indicator of a biologic state in a subject. With reference to the present subject matter, the biomarkers disclosed herein can be molecules that exhibit a change in expression to predict whether a subject would benefit from receiving IAP inhibitor treatment.

DETAILED DESCRIPTION OF THE INVENTION

To maximize the potential clinical benefit of a patient receiving an IAP inhibitor it is important to be able to select those patients who have tumors that are more likely to respond to an IAP inhibitor. The methods described herein are based upon the identification of a plurality of biomarkers which can be used to determine a patient's likelihood of benefiting from IAP inhibitor treatment. The biomarkers of the invention were purposefully optimized for routine clinical testing.

Biomarker

The biomarker(s) of the invention includes three or more of the following genes: CXLC10, CCL5, NFKBIA, HERC5, CDYL, STK39, MAPK14, TNF and RIPK1. By analyzing the expression level of three or more biomarkers identified above it is possible to select individuals having cancers in which the IAP inhibitors are likely to be therapeutically more effective.

The biomarkers of the invention include determining mRNA levels of CXLC10, CCL5, NFKBIA, HERC5, CDYL, MAPK14, TNF and RIPK1 (higher relative mRNA expression); and STK39 (lower relative mRNA expression). In one example, the expression profile can be a set of values representing mRNA levels, or ratios of expression levels, of three or more of the following genes CXLC10, CCL5, NFKBIA, HERC5, CDYL, STK39, MAPK14, TNF and RIPK1. In another example, the expression profile can be a set of values representing mRNA levels of STK39, TNF and RIPK1, or ratios of mRNA expression levels for these three genes. High or low mRNA expression can mean the amount of mRNA in a sample from an individual having cancer relative to a control sample or set of control samples. In another example, a level of higher expression of one of the three (TNF, RIPK1 or STK39) genes corresponding to the other within a sample from an individual having cancer will select individuals having cancers in which the IAP inhibitors are likely to be therapeutically more effective.

In another embodiment, the invention includes determining the mRNA expression of at least two markers selected from the group consisting of STX39, CXLC10, CCL5, NFK-BIA, HERC5, CDYL, and MAPK14. In one example, the two markers are CCL5 and STK39. In yet another example, the invention includes determining a level of expression of STK39.

IAP Inhibitors

Examples of IAP inhibitors for use in the present disclosure include any IAP inhibitor. In one example, the invention includes a compound of formula M-L-M', where M and M' are each independently a monomeric moiety of Formula (I)

wherein:
R$^1$ is (C$_1$-C$_4$)alkyl or hydrogen;
R$^2$ is hydrogen, (C$_1$-C$_4$)alkyl, halo-substituted (C$_1$-C$_4$) alkyl, (C$_3$-C$_6$)cycloalkyl, —CH$_2$—(C$_3$-C$_6$)cycloalkyl, benzyl, HO—(C$_1$-C$_4$)alkyl-, or CH$_3$NHC(O)—;
R$^3$ is (C$_1$-C$_4$)alkyl, halo-substituted (C$_1$-C$_4$)alkyl, or hydrogen;
or R$^2$ along with the nitrogen atom to which R$^2$ is attached is taken together with R$^3$ to form a 3- to 6-membered heterocyclic ring optionally containing 1 to 2 additional hetero-ring atoms each independently selected from N, O and S;
Q is (C$_1$-C$_4$)alkyl, (C$_1$-C$_4$)alkoxy, —OH, —C(O)—(C$_1$-C$_4$)alkyl, —O—C(O)—(C$_1$-C$_4$)alkyl, —NH$_2$, —NH—(C$_1$-C$_4$)alkyl, —N((C$_1$-C$_4$)alkyl)$_2$, —NH—C(O)—(C$_1$-C$_4$)alkyl, —NHSO(C$_1$-C$_4$)alkyl, —NHSO(phenyl), —N((C$_1$-C$_4$)alkyl)-SO(C$_1$-C$_4$)alkyl, —N((C$_1$-C$_4$)alkyl)-SO(phenyl), —NHSO$_2$(C$_1$-C$_4$)alkyl, —NHSO$_2$(phenyl), —N((C$_1$-C$_4$)alkyl)-SO$_2$(C$_1$-C$_4$)alkyl, or —N((C$_1$-C$_4$)alkyl)-SO$_2$(phenyl);
o is 0, 1, or 2;
A is a 6-membered heteroaryl ring containing at least one N ring heteroatom;
D is a bond, —C(O)—, —O—, —NH—, —S—, —S(O)—. —SO$_2$—, —N((C$_1$-C$_4$)alkyl)-, —N((C$_1$-C$_4$) alkyl-OH)—, —N((C$_3$-C$_6$)cycloalkyl)-, —NHC(O)—, —N((C$_1$-C$_4$)alkyl)C(O)—. —C(O)NH—, —C(O)—N ((C$_1$-C$_4$)alkyl)-, —N((C$_1$-C$_4$)alkyl-CO$_2$—(C$_1$-C$_4$) alkyl)-, —(C$_1$-C$_4$)alkylene, (C$_2$-C$_6$)alkenylene, —CH (OH)—, —C(O)—(C$_1$-C$_4$)alkylene, —NH—(C$_1$-C$_4$) alkylene, —S—(C$_1$-C$_4$)alkylene, —S(O)—(C$_1$-C$_4$) alkylene, —SO$_2$—(C$_1$-C$_4$)alkylene, —NHSO$_2$(C$_1$-C$_4$) alkylene, —NHSO(C$_1$-C$_4$)alkylene, or —CH(R)—, where R is NH$_2$, —NH((C$_1$-C$_4$)alkylene)phenyl), —NH (C$_1$-C$_4$)alkyl, —O((C$_1$-C$_4$)alkylene)phenyl) or —O(C$_1$-C$_4$)alkyl, wherein said ((C$_1$-C$_4$)alkylene)phenyl) or (C$_1$-C$_4$)alkyl is optionally substituted with halo;
A$^1$ is H, CF$_3$, phenyl, naphthyl, a partially or fully saturated (C$_3$-C$_6$)cycloalkyl, a 5- to 12 membered partially or fully saturated heterocycle containing 1 to 3 heteroatoms each independently selected from O, S or N, or a 5- to 10-membered heteroaryl containing 1 to 4 heteroatoms each independently selected from O, S or N,
where said phenyl, naphthyl and said heteroaryl are optionally substituted with 1 to 3 substituents each independently selected from halo, (C$_1$-C$_4$)alkyl, halo-substituted(C$_1$-C$_4$)alkyl, (C$_1$-C$_4$)alkoxy, —C(O)NHCH$_3$, —C(O)N(CH$_3$)$_2$, CN, or NO$_2$, and
where said heterocycle and said cycloalkyl are optionally fused to a phenyl or 6-membered heteroaryl containing 1 to 3 heteroatoms each independently selected from O, S or N, and where said heterocycle, said cycloalkyl, said fused heterocycle and said fused cycloakyl are optionally substituted with oxo, halo, (C$_1$-C$_4$)alkyl, halo-substituted(C$_1$-C$_4$)alkyl, or (C$_1$-C$_4$)alkoxy;

W is a bond, $(C_1-C_{10})$alkylene, $(C_1-C_{10})$alkenylene, $((C_1-C_4)$alkylene$)_m$-$(Y)_n$—B, $((C_1-C_4)$alkenylene$)_m$-$(Y)_n$—B, where m and n are each independently 0 or 1, Y is phenylene, naphthylene, a partially or fully saturated 3- to 6-membered cycloalkylene, 5- to 6-membered fully or partially saturated heterocyclene containing 1 to 3 heteroatoms each independently selected from O, S or N, or a 5- to 10-heteroarylene containing 1 to 4 heteroatoms each independently selected from O, S, or N, and B is a bond, —O—, $(C_1-C_4)$alkylene, or —(CH$_2$) (phenylene), where said $(C_1-C_{10})$alkylene, $(C_1-C_{10})$alkenylene, $(C_1-C_4)$alkylene, or $(C_1-C_4)$alkenylene moiety optionally contains an oxygen or nitrogen atom interspersed within the alkylene chain and is optionally substituted with oxo, —CF$_3$, phenyl, naphthyl, a 5- to 10-membered heteroaryl containing 1 to 4 heteroatoms each independently selected from O, S, or N, a partially or fully saturated 5- to 6-membered cycloalkyl, a 5- to 6-membered fully or partially saturated heterocycle containing 1 to 3 heteroatoms each independently selected from O, S or N, and/or 1 or more halo, where said partially or fully saturated heterocyclene is optionally substituted with 1 to 2 substituents each independently selected from oxo, $(C_1-C_4)$alkyl, or halo, where said heteroaryl or said heteroarylene is optionally substituted with 1 to 3 substituents selected from halo or $(C_1-C_4)$alkyl, and where said phenylene, said phenyl, said naphthyl, said naphthylene, said cycloalkylene, or said cycloalkyl is optionally substituted with 1 to 3 substituents each independently selected from halo, —CF$_3$, $(C_1-C_4)$alkyl, or $(C_1-C_4)$alkoxy, or when W is $((C_1-C_4)$alkylene$)_m$-$(Y)_n$—B or $((C_1-C_4)$alkenylene$)_m$-$(Y)_n$—B and L is NR$^5$—C(O)—X$^2$—C(O)—NR$^5$— or —NR$^5$—S(O)$_2$—X$^2$—S(O)$_2$—NR$^5$—, B is optionally taken together with R$^5$ along with the nitrogen to which R$^5$ is attached to form a heterocyclic ring selected from the group consisting of aziridinyl, azetidinyl, pyrrolidinyl, 1H-pyrrolyl, piperidinyl, 1H-indolyl, indolinyl, 1H-dihydroimidazolyl, 1H-imidazolyl, piperazinyl, hexahydropyrimidinyl, 1,2,3,4-tetrahydroquinolinyl, 1,2,3,4-tetrahydroisoquinolinyl, 5,6,7,8-tetrahydropyrido[3,4-b]pyrazinyl, oxazolidinyl, and thiazolidinyl, where said heterocyclic ring is optionally substituted with 1 to 3 substituents each independently selected from $(C_1-C_4)$alkyl, —OH, or oxo;

L is a linker group selected from the group consisting of —C(O)—NR$^5$—X$^1$—NR$^5$—C(O)—, —S(O)$_2$—NR$^5$—X$^1$—NR$^5$—S(O)$_2$—, —NR$^5$—C(O)—X$^2$—C(O)—NR$^5$—, and —NR$^5$—S(O)$_2$—X$^2$—S(O)$_2$—NR$^5$—, where R$^5$ is hydrogen, $(C_1-C_4)$alkyl, benzyl, or cyclohexyl; and X$^1$ is
(i) a bond,
(ii) $(C_1-C_{10})$alkylene, $(C_2-C_{10})$alkenylene, $(C_2-C_{10})$alkynylene, $((C_1-C_{10})$alkylene$)$-$(O(C_1-C_6)$alkylene$)_p$-, or $(C_1-C_{10})$alkylene-NH$(C_1-C_6)$alkylene, where p is 0, 1 or 2,
(iii) phenylene, napthylene, fluorenylene, 9H-fluoren-9-onylene, 9,10-dihydroanthracenylene, anthracen-9,10-dionylene, a partially or fully saturated $(C_3-C_8)$ cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5-C_6)$cycloalkyl,
(iv) (phenylene)-G-(phenylene), where G is a bond, O, S, —NH—, —N=N—, —S=S—, —SO$_2$—, $(C_1-C_6)$alkylene, $(C_2-C_6)$alkenylene, $(C_2-C_{10})$alkynylene, $(C_3-C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl,
(v) $((C_1-C_6)$alkylene$)_r$-Z$^1$—$((C_1-C_6)$alkylene$)_s$, or $((C_1-C_6)$alkenylene$)_r$-Z$^1$—$((C_1-C_6)$alkenylene$)_s$, where r and s are each independently 0, 1, or 2; and Z$^1$ is —O—, —N=N—, $(C_3-C_6)$cycloalkylene, phenylene, a 5- to 6-membered partially or fully saturated heterocyclene containing 1 to 3 heteroatoms each independently selected from O, S or N, or a 5-to-6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5-to-6-membered heteroarylene containing 1 to 3 heteroatoms each independently selected from O, S or N, or
(vi) $(C_1-C_{20})$alkylene or —NH—$((C_1-C_{20})$alkylene)-NH—, where said alkylene contains 1 to 6 oxygen atoms interspersed within the alkylene chain and optionally 1 to 2 phenylene groups interpersed within the alkylene chain;
or X$^1$ is optionally taken together with both R$^5$ groups along with the nitrogens to which both R$^5$ groups are attached to form an 2,6-diazaspiro[3.3]heptane;

X$^2$ is
(i) a bond or —O—, —NH—, or —N($(C_1-C_4)$alkyl)-,
(ii) $(C_1-C_{10})$alkylene, —(O$(C_1-C_6)$alkylene$)_p$-, —$((C_1-C_6)$alkylene O$)_q$—, —O—$((C_1-C_6)$alkylene O$)_q$—, $(C_2-C_{10})$alkenylene, $((C_1-C_{10})$alkylene)-(O$(C_1-C_6)$alkylene$)_p$-, —O—$((C_1-C_{10})$alkyl)-O—, or $(C_1-C_{10})$alkylene-NH$(C_1-C_6)$alkylene, or $(C_2-C_{10})$alkynylene, where p and q are each independently 1, 2, or 3,
(iii) phenylene, napthylene, fluorenylene, 9H-fluoren-9-onylene, 9,10-dihydroanthracenylene, anthracen-9,10-dionylene, a partially or fully saturated $(C_3-C_8)$ cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5-C_6)$cycloalkyl,
(iv) (phenylene)-G-(phenylene), or —O-(phenylene)-G-(phenylene)-O—, where G is a bond, O, S, —NH—, —N=N—, —S=S—, —SO$_2$—, $(C_1-C_6)$alkylene, $(C_2-C_6)$alkenylene, $(C_3-C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl,
(v) $((C_1-C_6)$alkylene$)_r$-Z$^1$—$(C_1-C_6)$alkylene$)_s$, $((C_1-C_6)$alkenylene$)_r$-Z$^1$—$((C_1-C_6)$alkenylene$)_s$, or —(O$(C_1-C_3)$alkylene$)_u$-Z$^2$—$((C_1-C_3)$alkylene O$)_v$—, where r, s, u, and v are each independently 0, 1, or 2; and $Z^1$ and $Z^2$ are —O—, —N=N—, $(C_3-C_6)$cycloalkylene, phenylene, a 5- to 6-membered partially or fully saturated heterocyclene containing 1 to 3 heteroatoms each independently selected from O, S or N, or a 5-to-6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from 0, S or N, or a 5-to-6-membered heteroarylene containing 1 to 3 heteroatoms each independently selected from O, S or N, or (vi) $(C_1-C_{20})$alkyl or —NH—$((C_1-C_{20})$alkylene)-NH—, where said alkylene contains 1 to 6 oxygen atoms interspersed within the alkylene chain and optionally 1 to 2 phenylene groups interspersed within the alkylene chain;

where said group (ii) moieties of $X^1$ and $X^2$ are each independently substituted with one or more fluoro atoms, or 1 to 2 substituents each independently selected from halo, oxo, amino, phenyl, naphthyl, $(C_3-C_6)$ cycloalkyl, or 5- to 6-membered heterocycle containing 1 to 3 heteroatoms each independently selected from O, N or S, where said phenyl, said cycloalkyl, and said heterocycle are optionally substituted with 1 to 3 substituents each independently selected from halo, $(C_1-C_4)$alkyl, or trifluoromethyl, where said group (iii) and (iv) moieties of $X^1$ and $X^2$ are optionally substituted with 1 to 4 substituents each independently selected from $(C_1-C_4)$alkyl, $(C_1-C_4)$alkoxy, halo, amino, —OH, benzyl, or a fused 5- to 6-membered cycloalkyl, where said $(C_1-C_4)$alkyl, said $(C_1-C_4)$ alkoxy, and said fused cycloalkyl are optionally substituted with 1 to 3 substituents selected from halo, $(C_1-C_4)$alkyl, where said group (v) moieties of $X^1$ and $X^2$ are optionally substituted with 1 to 3 substituents each independently selected from halo, hydroxy, oxo, amino, $(C_1-C_4)$alkyl, $(C_1-C_4)$alkoxy, or phenyl;

or a pharmaceutically acceptable salt thereof.

In another example, the IAP inhibitor compound can be a compound of Formula M-L-M', wherein M and M' are each independently a monomeric moiety of Formula (I)

(I)

wherein, $R^1$ is $(C_1-C_4)$alkyl, deuterated methyl, or hydrogen;

$R^2$ is $(C_1-C_4)$alkyl or hydrogen;

$R^3$ is $(C_1-C_4)$alkyl or hydrogen, or $R^1$ or $R^2$ along with the nitrogen to which $R^1$ or $R^2$ is attached is taken together with $R^3$ to form an aziridinyl, azetidinyl, pyrrolidinyl, or piperidinyl;

$R^4$ is (i) $(C_1-C_{10})$alkyl, $(C_2-C_{10})$alkenyl, $(C_2-C_{10})$alkynyl, $(C_3-C_6)$cycloalkyl, phenyl, a 3- to 7-membered heterocycle containing 1 to 3 heteroatoms each independently selected from O, N or S, or a 5- to 9-membered heteroaryl containing 1 to 3 heteroatoms each independently selected form O, N or S, or (ii) $R^{4a}$—$(C_1-C_6)$alkylene, where $R^{4a}$ is $(C_3-C_6)$cycloalkyl, phenyl, a 3- to 7-membered heterocycle containing 1 to 3 heteroatoms each independently selected from O, N or S, or a 5- to 9-membered heteroaryl containing 1 to 3 heteroatoms each independently selected form O, N or S, where said $R^4$ and said $R^{4a}$ are optionally substituted with 1 to 3 substituents selected from halo, hydroxyl, —SH, —$CO_2H$, $(C_1-C_4)$alkyl, halo-substituted$(C_1-C_4)$alkyl, $(C_1-C_4)$alkoxy, $(C_1-C_4)$alkyl-S—, —$SO_2$, —$NH_2$ or —$NO_2$, and where 1 of the ring members of said cycloalkyl and said heterocycle moieties are optionally replaced with oxo or thione;

A, B, and D are $CR^5$, and E is N,

A, B and E are $CR^5$ and D is N,

A, D and E are $CR^5$, and B is N,

B, D and E are $CR^5$, and A is N,

A and B are both N, and D and E are both $CR^5$,

A and E are both N, and B and D are both $CR^5$, or

B and E are both N, and A and D are both $CR^5$, where $R^5$ are each independently selected from H, F, —$CH_3$ or —$CF_3$;

V is selected from moieties of Formula (1a), (1b), (1c), (1d), (1e), (1f), (1g), (1h), (1i), (1j), or (1k)

(1a)

(1b)

(1c)

where * indicates the point of attachment to L,
$R^{6a}$ and $R^{6b}$ are each independently H, $(C_1\text{-}C_3)$alkyl, Cl, or CN, where at least one of
$R^{6a}$ and $R^{6b}$ is H or $(C_1\text{-}C_3)$alkyl;
W is a bond or $(C_1\text{-}C_4)$alkylene;
$R^7$ are each independently halo, —CH$_3$, —CF$_3$, —CN or —OCH$_3$;
p is 0, 1, 2, 3 or 4 for formula (1a) or (1e),
p is 0, 1, 2 or 3 for formula (1b), (1c), (1d), (1f), (1i) or (1j),
p is 0, 1 or 2 for formula (1g) or (1h);
L is —NR$^8$—X$^1$—NR$^8$—, where each R$^8$ is independently selected from H, $(C_1\text{-}C_4)$alkyl, or halo-substituted$(C_1\text{-}C_4)$alkyl and X$^1$ is
(i) a bond,
(ii) $(C_1\text{-}C_{10})$alkylene, $(C_2\text{-}C_{10})$alkenylene, $(C_2\text{-}C_{10})$alkynylene, $((C_1\text{-}C_{10})$alkylene)-$(O(C_1\text{-}C_6)$alkylene)$_q$-, or $(C_1\text{-}C_{10})$alkylene-NH$(C_1\text{-}C_6)$alkylene, where q is 0, 1 or 2,
(iii) phenylene, napthylene, fluorenylene, 9H-fluoren-9-onylene, 9,10-dihydroanthracenylene, anthracen-9,10-dionylene, a partially or fully saturated $(C_3\text{-}C_8)$cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5\text{-}C_6)$cycloalkyl,
(iv) (phenylene)-G-(phenylene), where G is a bond, O, S, —NH—, —N═N—, —S═S—, —SO$_2$—, $(C_1\text{-}C_6)$alkylene, $(C_2\text{-}C_6)$alkenylene, $(C_2\text{-}C_{10})$alkynylene, $(C_3\text{-}C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl,
(v) $((C_1\text{-}C_6)$alkylene)$_r$-Z$^1$—$((C_1\text{-}C_6)$alkylene)$_s$, or $((C_1\text{-}C_6)$alkenylene)$_r$-Z$^1$—$((C_1\text{-}C_6)$alkenylene)$_s$, where r and s are each independently 0, 1, or 2; and Z$^1$ is —O—, —N═N—, $(C_3\text{-}C_6)$cycloalkylene, phenylene, bisphenylene, a 5- to 6-membered partially or fully saturated heterocyclene containing 1 to 3 heteroatoms each independently selected from O, S or N, or a 5-to-6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5-to-6-membered heteroarylene containing 1 to 3 heteroatoms each independently selected from O, S or N, or
(vi) $(C_1\text{-}C_{20})$alkylene or —NH—$((C_1\text{-}C_{20})$alkylene)-NH—, where said alkylene contains 1 to 6 oxygen atoms interspersed within the alkylene chain and optionally 1 to 2 phenylene groups interspersed within the alkylene chain;

or $X^1$ is optionally taken together with one or both $R^8$ groups along with the nitrogen to which the $R^8$ group is attached to form a 4- to 14-membered heterocyclene, (4- to 6-membered heterocyclyl)-($C_1$-$C_6$)alkylene-(4- to 6-membered heterocyclyl), or bis-(4- to 6-membered heterocyclene, where said heterocyclene and said heterocyclyl moieties optionally contain 1 to 3 additional heteroatoms selected from O, S and N, and $X^1$ and $R^8$ are optionally substituted with oxo or 1 to 3 substituents each independently selected from hydroxyl or ($C_1$-$C_4$)alkyl;

where said group (ii) moieties of $X^1$ are each independently substituted with one or more fluoro atoms, or 1 to 2 substituents each independently selected from halo, oxo, amino, phenyl, naphthyl, ($C_3$-$C_6$) cycloalkyl, or 5- to 6-membered heterocycle containing 1 to 3 heteroatoms each independently selected from O, N or S, where said phenyl, said cycloalkyl, and said heterocycle are optionally substituted with 1 to 3 substituents each independently selected from halo, ($C_1$-$C_4$)alkyl, or trifluoromethyl, where said group (iii) and (iv) moieties of $X^1$ are optionally substituted with 1 to 4 substituents each independently selected from ($C_1$-$C_4$)alkyl, ($C_1$-$C_4$)alkoxy, halo, amino, —OH, benzyl, or a fused 5- to 6-membered cycloalkyl, where said ($C_1$-$C_4$)alkyl, said ($C_1$-$C_4$)alkoxy, and said fused cycloalkyl are optionally substituted with 1 to 3 substituents selected from halo, or ($C_1$-$C_4$)alkyl, where said group (v) moieties of $X^1$ are optionally substituted with 1 to 3 substituents each independently selected from halo, hydroxy, oxo, amino, ($C_1$-$C_4$)alkyl, ($C_1$-$C_4$)alkoxy, or phenyl;

or a pharmaceutically acceptable salt thereof.

In yet another example, the IAP inhibitor compound can include a compound of formula (IV)

IV wherein
$R_1$ and $R_3$ are each independently methyl or ethyl;
$R_2$ is H, methyl, ethyl, chloromethyl, dichloromethyl or trifluoromethyl;
$R_4$ is $C_1$-$C_4$alkyl or $C_3$-$C_7$ cycloalkyl;
$R_5$ is H;
U is a structure of formula (V)

V where
(a) X is N;
$R_6$, $R_6'$, $R_7$ and $R_7'$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, where $Ar_1$ and $Ar_2$ are each independently a substituted or unsubstituted phenyl or het, and D is $C_1$ alkyl which is optionally substituted with halo, where the phenyl or the het of $Ar_1$ is attached to both (Rb)n and D, and the phenyl or the het of $Ar_2$ is attached to both D and $R^5$;

(b) X is N;
$R_6$, $R'_6$, $R_7$, and $R'_7$ are H; or
$R_6$ is —C(O)—$C_1$-$C_4$alkyl-phenyl and $R'_6$, $R_7$, and $R'_7$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, wherein $Ar_1$ and $Ar_2$ are each independently a substituted or unsubstituted phenyl or het, and D is N(Rh), where Rh is H, Me, —CHO, —$SO_2$, —C(O), —CHOH, —$CF_3$ or —$SO_2CH_3$, where the phenyl or the het of $Ar_1$ is attached to both (Rb)n and D, and the phenyl or the het of $Ar_2$ is attached to both D and $R^5$;

(c) X is N;
$R_6$, $R'_6$, $R_7$, and $R'_7$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, where $Ar_1$ and $Ar_2$ are each independently a substituted or unsubstituted phenyl or het, and D is —O—, where the phenyl or the het of $Ar_1$ is attached to both (Rb)n and D, and the phenyl or the het of $Ar_2$ is attached to both D and $R^5$; or (d) X is N;
$R_6$, $R'_6$, $R_7$, and $R'_7$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, where $Ar_1$ and $Ar_2$ are each independently a substituted or unsubstituted phenyl or het, and D is S, S(O), or S(O)$_2$, where the phenyl or the het of $Ar_1$ is attached to both (Rb)n and D, and the phenyl or the het of $Ar_2$ is attached to both D and $R^5$;

(e) X is N;
$R_6$, $R'_6$, $R_7$, and $R'_7$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$;

$Ar_1$ and $Ar_2$ are each independently a substituted or unsubstituted phenyl or het, and D is C(O), where the phenyl or the het of $Ar_1$ is attached to both (Rb)n and D, and the phenyl or the het of $Ar_2$ is attached to both D and $R^5$;

or a pharmaceutically acceptable salt thereof.

Specific examples of compounds include:

(S,S,S)—N,N'-(3,3'-(ethane-1,2-diylbis(oxy))bis(propane-3,1-diyl))bis(1-(5-((S)-1-((S)-3-methyl-2-((S)-2-(methylamino)-propanamido)butanoyl)pyrrolidin-2-yl)pyridin-3-yl)-1H-indole-4-carboxamide);

(S,S,S)—N,N'-(1,4-phenylenebis-(methylene))bis(1-(5-((S)-1-((S)-3-methyl-2-((S)-2-(methylamino)-propanamido)butanoyl)pyrrolidin-2-yl)pyridin-3-yl)-1H-indole-4-carboxamide);

(S,S,S)—N,N'-(propane-1,3-diyl)bis(1-(5-((S)-1-((S)-3-methyl-2-((S)-2-(methylamino)propanamido)butanoyl)pyrrolidin-2-yl)pyridin-3-yl)-1H-indole-4-carboxamide);

(S,S,S)—N,N'-((1S,2S)-cyclohexane-1,2-diyl)bis(1-(5-((S)-1-((S)-3-methyl-2-((S)-2-(methylamino)propanamido)butanoyl)pyrrolidin-2-yl)pyridin-3-yl)-1H-indole-4-carboxamide); and (S,S,S)—N,N'-(3,3'-(ethane-1,2-diylbis(oxy))bis(propane-3,1-diyl))bis(1-(5-((S)-1-((S)-3-methyl-2-((S)-2-(trideuteromethylamino)propanamido)butanoyl)pyrrolidin-2-yl)pyridin-3-yl)-1H-indole-4-carboxamide);

Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and

Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

(S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propion or a pharmaceutically acceptable salt thereof.

Examples of other IAP inhibitors includes compounds disclosed in WO 05/097791 published on Oct. 20, 2005, which is hereby incorporated into the present application by reference. A preferred compound within the scope of formula (I) is N-[1-cyclohexyl-2-oxo-2-(6-phenethyl-octahydro-pyrrolo[2,3-c]pyridin-1-yl-ethyl]-2-methylamino-propionamide, hereinafter compound II.

Examples of other IAP inhibitors include those disclosed in WO2008134679 concerning and US20060014700. In one example, the compound is GDC-0152.

1 (GDC-0152)

Additional IAP inhibitors include compounds disclosed in WO 04/005284, PCT/US2006/013984, PCT/US2006/021850 all of which are hereby incorporated into the present application by reference.

Other IAP inhibitor compounds for use in the present disclosure include those disclosed in WO 06/069063, WO 05/069888, US2006/0014700, WO 04/007529, US2006/0025347, WO 06/010118, WO 05/069894, WO 06/017295, WO 04/007529, WO 05/094818.

In each case where citations of patent applications are given above, the subject matter relating to the compounds is hereby incorporated into the present application by reference. Comprised are likewise the pharmaceutically acceptable salts thereof, the corresponding racemates, diastereoisomers, enantiomers, tautomers, as well as the corresponding crystal modifications of above disclosed compounds where present, e.g., solvates, hydrates and polymorphs, which are disclosed therein. The compounds used as active ingredients in the combinations of the disclosure can be prepared and administered as described in the cited documents, respectively. Also within the scope of this disclosure is the combination of more than two separate active ingredients as set forth above, i.e., a pharmaceutical combination within the scope of this disclosure could include three active ingredients or more.

Preparation of Samples

Any appropriate test sample of cells taken from an individual having a proliferative disease can be used. Generally, the test sample of cells or tissue sample will be obtained from the subject with cancer by biopsy or surgical resection. A sample of cells, tissue, or fluid may be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample or a frozen tissue sample. Once a sample of cells or sample of tissue is removed from the subject with cancer, it may be processed for the isolation of RNA or protein using techniques well known in the art and as described below.

An example of extraction of RNA from a biopsy taken from a patient with cancers can include, for example, guanidium thiocyanate lysis followed by CsCl centrifugation (Chirgwin, et al., Biochemistry 18:5294-5299, 1979). RNA from single cells may be obtained as described in methods for preparing cDNA libraries from single cells (see, e.g., Dulac, Curr. Top. Dev. Biol. 36:245, 1998; Jena, et al., J. Immunol. Methods 190:199, 1996). In one embodiment, the RNA population may be enriched for sequences of interest, as detailed in Table 1. Enrichment may be accomplished, for example, by random hexamers and primer-specific cDNA synthesis, or multiple rounds of linear amplification based on cDNA synthesis and template-directed in vitro transcription (see, e.g., Wang, et al., Proc. Natl. Acad. Sci. USA 86:9717, 1989; Dulac, et al., supra; Jena, et al., supra). Other methods of isolating RNA from a sample are known in the art and include Trizol (Invitrogen), Guanidinium thiocyanate-phenol-chloroform extraction, PureLink Micro-to-Midi Total RNA Purification System (invitrogen), RNeasy kit (Qiagen), Oligotex kit (Qiagen), PureYield™ RNA Midiprep (Promega), PolyATtract System 1000 (Promega), Maxwell® 16 System (Promega), SV Total RNA Isolation (Promega), ToTALLY RNA™ Kit (Ambion), Poly(A)Purist™ Kit (Ambion) and any other methods. Methods for extracting and analysing an RNA sample are disclosed in Molecular Cloning, A Laboratory Manual (Sambrook and Russell (ed.), 3rd edition (2001), Cold Spring Harbor Laboratory Press, Cold Spring Harbor, N.Y., USA.

The mRNA expression profile can be performed on a biopsy taken from a subject such as fresh tissue, frozen tissue, tissue processed in formalin (FFPE) or other fixatives. In particular, where the sample is an FFPE sample, RNA is extracted from FFPE sections using the Qiagen RNeasy FFPE extraction kit (Qiagen), and reverse transcribed to cDNA using random hexamers and ABI's High Capacity cDNA archive kit (Applied Biosystems, Foster City, Calif.).

The subject with a tumor or cancer will generally be a mammalian subject such as a primate. In an exemplary embodiment, the subject is a human. As used herein the terms patient and subject are synonymous.

Any cancer or tumor can be screened according to the methods of the invention and include, but are not limited to, colon cancer, lung cancer, pancreatic cancer, gastric cancer, prostate cancer, and hepatocellular carcinoma, basal cell carcinoma, breast cancer, bone sarcoma, soft tissue sarcoma, chronic myeloid leukemia, acute myeloid leukemia, hematological cancer, medulloblastoma, rhabdomyosaracoma, neuroblastoma, pancreatic cancer, ovarian cancer, meningioma, glioblastoma, astrocytoma, melanoma, stomach cancer, esophageal cancer, biliary tract cancer, prostate cancer, small cell lung cancer, non-small cell lung cancer, glial cell cancer, multiple myeloma, colon cancer, neuroectodermal tumor, neuroendocrine tumor, mastocytoma and Gorlin syndrome, glioma, colorectal cancer, GIST, gastro-esophageal cancer, myeloproliferative neoplasia and an acute leukemia.

Detection of Expression of the Biomarker

In one example, the method includes determining expression of three or more of the genes CXLC10, CCL5, NFKBIA, HERC5, CDYL, STK39, MAPK14, TNF and RIPK1 in a sample of interest. Specifically the invention includes determining a level of expression of TNF and RIPK1 and one or more of the following biomarkers CXLC10, CCL5, NFKBIA, HERC5, CDYL, STK39 and MAPK14 in the sample of interest. In another example, the invention includes determining a level of expression of STK39 and CCL5. In yet another example, the invention includes determining a level of expression of STK39. The gene sequences of interest can be detected using agents that can be used to specifically detect the gene, for example, RNA transcribed from the gene or polypeptides encoded by the gene.

In one embodiment, the method includes: providing a nucleic acid probe comprising a nucleotide sequence, for example, at least 10, 15, 25 or 40 nucleotides, and up to all or nearly all of the coding sequence which is complementary to a portion of the coding sequence of a nucleic acid sequence of CXLC10, CCL5, NFKBIA, HERC5, CDYL, STK39, MAPK14, TNF and RIPK1; obtaining a tissue sample from a mammal having a cancerous cell; contacting the nucleic acid probe under stringent conditions with RNA obtained from a biopsy taken from a patient with cancer(e.g., in a Northern blot, in situ hybridization assay, PCR etc); and determining the amount of hybridization of the probe with RNA. Nucleic acids may be labeled during or after enrichment and/or amplification of RNAs.

The biomarkers CXLC10, CCL5, NFKBIA, HERC5, CDYL, STK39, MAPK14, TNF and RIPK1 are intended to also include naturally occurring sequences including allelic variants and other family members. The biomarkers of the invention also include sequences that are complementary to those listed sequences resulting from the degeneracy of the code and also sequences that are sufficiently homologous and sequences which hybridize under stringent conditions to the genes of the invention.

Conditions for hybridization are known to those skilled in the art and can be found in Current Protocols in Molecular Biology, John Wiley and Sons, N.Y. (1989), 6.3.1-6.3.6. A preferred, non-limiting example of highly stringent hybridization conditions are hybridization in 6× sodium chloride/sodium citrate (SSC) at about 45 degrees centigrade followed by one or more washes in 0.2×SSC, 0.1 percent SDS at 50-65 degrees centigrade. By "sufficiently homologous" it is meant a amino acid or nucleotide sequence of a biomarker which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 50 percent homology, at least about 60 percent homology, at least about 70 percent, at least about 80 percent, and at least about 90-95 percent homology across the amino acid sequences of the domains are defined herein as sufficiently homologous. Furthermore, amino acid or nucleotide sequences at least about 50 percent homology, at least about 60-70 percent homology, at least about 70-80 percent, at least about 80-90 percent, and at least about 90-95 percent and share a common functional activity are defined herein as sufficiently homologous.

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990)

Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs (version 2.0) of Altschul, et al. (1990) J. MoI. Biol. 215:403-10. BLAST nucleotide searches can be performed with the NBLAST program, score=100, wordlength=12 to obtain nucleotide sequences homologous to TRL nucleic acid molecules of the invention. BLAST protein searches can be performed with the XBLAST program, score=50, wordlength=3 to obtain amino acid sequences homologous to the protein sequences encoded by the genes/oligonucleotides listed in Table 1. To obtain gapped alignments for comparison purposes, Gapped BLAST can be utilized as described in Altschul et al., (1997) Nucleic Acids Research 25(17):3389-3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the ALIGN algorithm of Myers and Miller, CABIOS (1989). When utilizing the ALIGN program for comparing amino acid sequences, a PAM120 weight residue table, a gap length penalty of 12, and a gap penalty of 4 can be used.

The present invention includes measuring the expression of three or more genes CXLC10, CCL5, NFKBIA, HERC5, CDYL, STK39, MAPK14, TNF and RIPK1 in a tumor biopsy taken from a subject suffering from cancer. The expression levels can be analyzed and used to generate a score which can be used to differentiate those patients having a tumor that is likely to be responsive to an IAP inhibitor versus those who are likely not to be.

In one embodiment, the method of the invention includes measuring any three of CXLC10, CCL5, NFKBIA, HERC5, CDYL, STK39, MAPK14, TNF and RIPK1 listed in Table 1. In another embodiment, the method of the invention includes measuring at least at least four, at least five, at least six, at least seven, or at least eight, or at least nine of the biomarkers described herein.

TABLE 1

| HUGO official gene symbol | HUGO approved name | HGNC ID | UGID | UniGene | Expression level |
|---|---|---|---|---|---|
| CXLC10 | chemokine (C-X-C motif) ligand 10 | 10637 | UGID: 2139480 | Hs.632586 | Increased |
| CCL5 | chemokine (C-C motif) ligand 5 | 10632 | UGID: 905568 | Hs.514821 | Increased |
| NFKBIA | nuclear factor of kappa light polypeptide gene enhancer in B-cells inhibitor, alpha | 7797 | UGID: 140532 | Hs.81328 | Increased |
| HERC5 | HECT and RLD domain containing E3 ubiquitin protein ligase 5 | 24368 | UGID: 135264 | Hs.26663 | Increased |
| CDYL | Chromodomain protein, Y-like | 1811 | UGID: 172621 | Hs.269092 | Increased |
| STK39 | serine threonine kinase 39 | 17717 | UGID: 174166 | Hs.276271 | Decreased |
| MAPK14 | Mitogen-activated protein kinase 14 | 6876 | UGID: 700392 | Hs.485233 | Increased |
| TNF | tumor necrosis factor | 11892 | UGID: 167910 | Hs.241570 | Increased |
| RIPK1 | Receptor (TNFRSF)-interacting serine-threonine kinase 1 | 10019 | UGID: 910589 | Hs.519842 | Increased |

The biomarkers of the invention also include any combination of genes identified in Table 1 whose level of expression or gene product serves as a predictive biomarker. The biomarkers of the invention, including their gene sequence, are known in the art.

In the method of the invention the level of expression of three or more genes as described in Table 1 is measured and analyzed and compared to a control. The control for comparison can be determined by one skilled in the art. In one example, the control is determined by choosing a value that serves as a cut-off value. For example, the value can be a value that differentiates between e.g., those test samples that have an increase in three or more genes as described in Table 1 from those that do not show an increase in three or more genes as described. In another example, the gene expression profile of a biomarker of the invention is compared to the gene expression profile of a control set of samples in which thresholds for high and low expression have been characterized (for example as percentiles).

In a particular embodiment of the invention, the control is predetermined and a score is generated which can be used to select those subjects having a tumor that is likely to show responsiveness to an IAP inhibitor.

The biomarkers of the invention can be measured using any method known in the art such as reverse Transcriptase PCR (RT-PCR). The method includes isolating mRNA using any technique known in the art and described above, e.g., by using a purification kit, buffer set and protease from commercial manufacturers, such as Qiagen. The reverse transcription step is typically primed using specific primers, random hexamers, or oligo-dT primers, depending on the circumstances and the goal of expression profiling and the cDNA derived can then be used as a template in the subsequent PCR reaction. TaqMan® RT-PCR can then be performed using, e.g., commercially available equipment.

The isolated mRNA can then be further analyzed using any method known in the art such as microarray analysis, quantitative ('real-time') PCR, northern blotting, and nuclease protection assay. In one example, real time quantitative PCR is used which measures PCR product accumulation through a dual-labeled fluorigenic probe (e.g., using TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al, Genome Research 6:986-994 (1996). In a real time PCR assay a positive reaction is detected by accumulation of a fluorescent signal. The Ct (cycle threshold) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample). Most real time assays undergo 40 cycles of amplification.

In another example, microarrays are used which include one or more probes corresponding to three or more of genes CXLC10, CCL5, NFKBIA, HERC5, CDYL, STK39, MAPK14, TNF and RIPK1. Use of a microarray results in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

In another example, a TaqMan® Low Density Array (TLDA) card can be used which can include one or more probes corresponding to three or more of genes CXLC10, CCL5, NFKBIA, HERC5, CDYL, STK39, MAPK14, TNF and RIPK1. This method uses a microfluidic card that performs simultaneous real time PCR reactions.

In one example, the method of detection utilizes an array scanner that is commercially available (Affymetrix, Santa Clara, Calif.), for example, the 417Arrayer, the 418Array Scanner, or the Agilent GeneArray Scanner. This scanner is controlled from a system computer with an interface and easy-to-use software tools. The output may be directly imported into or directly read by a variety of software applications. Scanning devices are described in, for example, U.S. Pat. Nos. 5,143,854 and 5,424,186.

Data Analysis

To facilitate the sample analysis operation, the data obtained by the reader from the device may be analyzed using a digital computer. Typically, the computer will be appropriately programmed for receipt and storage of the data from the device, as well as for analysis and reporting of the data gathered, for example, subtraction of the background, verifying that controls have performed properly, normalizing the signals, interpreting fluorescence data to determine the amount of hybridized target, normalization of background, and the like.

Kits

The invention further provides kits for determining the expression level of the biomarkers described herein. The kits may be useful for determining who will benefit from treatment with an IAP inhibitor. A kit can comprise probes of genes identified in Table 1 can be used to measure gene expression of a test sample. In one embodiment, the kit comprises a computer readable medium which includes expression profile analysis software capable of being loaded into the memory of a computer system and which can convert the measured expression values into a risk score. A kit may further comprise nucleic acid controls, buffers, and instructions for use.

Administration

The IAP inhibitors described herein can be selectively administered in therapeutically effective amounts via any of the usual and acceptable modes known in the art, either singly or in combination with one or more therapeutic agents based on the individual having been determined to be more likely to respond to IAP inhibitors based on the biomarkers disclosed herein. A therapeutically effective amount may vary widely depending on the severity of the disease, the age and relative health of the subject, the potency of the compound used and other factors.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

Example 1

Biomarkers for IAP Response

We used a statistical framework that integrates pharmacological data together with genetic and mRNA expression data in order to develop biomarkers for predicting response to IAP inhibitors. Using genomic data generated as part of the Cancer Cell Line Encyclopedia collection (Barretina J S, Caponigro G, Stransky N et al (2012) Nature; 483:603-7), we assembled gene copy number, mRNA expression and mutation data into a single matrix. Single agent cellular activity of various IAP antagonists was assessed against a panel of >500 tumor cell lines using a 72 hour proliferation assay. We classified these cell lines into sensitive, intermediate and refractory classes based on the distribution of IC50 data and manual curation of individual responses. A statistical test was applied in order to identify genomic "features" that could differentiate IAP antagonist-sensitive cell lines from refractory lines. Among the top-ranked genes showing differential mRNA expression were TNF and RIPK1, two genes with evidence for apoptotic response to IAP antagonists based on previous experimental studies involving one or a few cell lines. We are thus able to extend prior observations on limited experiments systematically to a large set of data and identified an additional set of seven genes (CXLC10, CCL5, NFKBIA, HERC5, CDYL, STK39 and MAPK14), whose mRNAs were differentially expressed in sensitive compared refractory lines.

We built a predictive machine learning model using the Naive Bayes classifier based on the 9-gene signature as well as a 2-gene TNF/RIPK1 signature. These predictive models significantly increase the cell line response rate to IAP antagonists as illustrated by the predictive performance (Area under the ROC curve or AUC) in Table 2. At several model cutoff regimes, this translates to a two- to three-fold increase in response rate to (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide, one of the IAP antagonists in our series, compared to random or "all-comers" cell lines where no selection is applied. For example, at model cutoffs optimized to obtain balanced performance between sensitivity and specificity for each model, the signatures yielded response rates of 16-18% in cross-validation compared to 8% response rate at random without any selection. This improved response rate was further validated in independent experimental testing of a compound-naive set of cell lines that were predicted to be sensitive (AUCs in Table 2).

TABLE 2

| Model | AUC (Area under the ROC curve) performance | Sample Set Context |
| --- | --- | --- |
| 2-gene | 0.81 | Cross-validation within cell lines |
| 3-gene | 0.79 | |
| 9-gene | 0.75 | |
| 2-gene | 0.61 | New, independent cell line test set |
| 3-gene | 0.60 | |
| 9-gene | 0.76 | |

Figure 1:
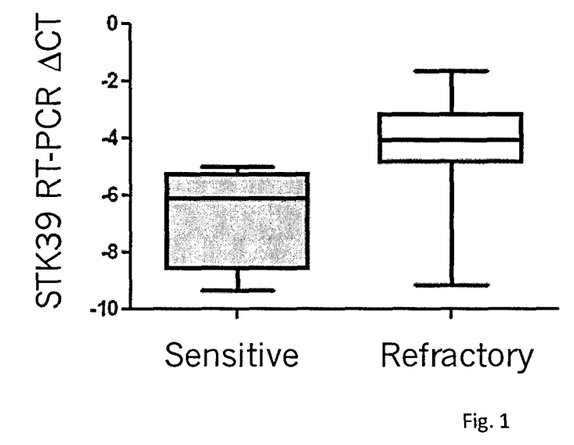
FIG. 1 shows a graph illustrating mean expression of STK39 mRNA measured by quantitative RT-PCR is lower in primary human tumors grown as xenografts in mice that are sensitive (gray) to (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide compared to refractory (white) tumors.

In addition, (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide has been tested for single agent activity in 55 patient-derived tumor models representing triple negative breast cancer, NSCLC and pancreatic cancer models. A range of responses were observed ranging from tumor regression to no effect. We observed that the 2-gene, 3-gene and 9-gene signatures can enrich for response at a rate consistent with the cell line data (Table 3, thus providing an independent in vivo validation for the signature. For example, at model cutoffs optimized to obtain balanced performance between sensitivity and specificity, the signatures yielded response rates of ~30% compared to 11% response rate at random. Among the seven novel candidate genes above, we found that lower levels of STK39 show strong correlation with (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide response in vivo (FIG. 1). Results from the xenograft study showed that the TNF, RIPK1 and STK39 ("3-gene" signature) performed surprisingly well in predicting (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide response in vivo (Table 3).

TABLE 3

| Model | AUC (Area under the ROC curve) performance | Sample Set Context |
| --- | --- | --- |
| 2-gene | 0.86 | Independent xenograft test set |
| 3-gene | 0.93 | |
| 9-gene | 0.87 | |

This set of three mRNAs was also shown to predict response to another TAP antagonist.

Figure 2:
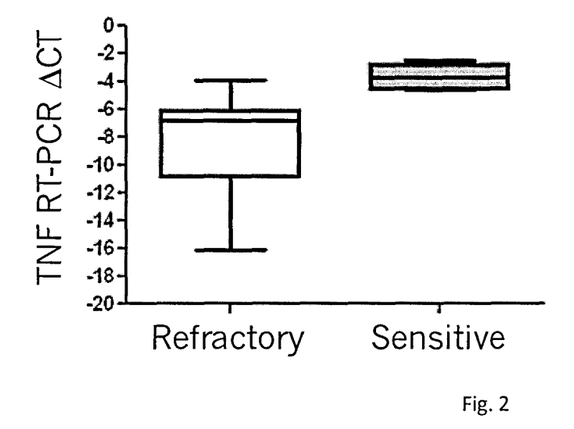
FIG. 2 shows a graph illustrating mean expression of TNF mRNA measured by quantitative RT-PCR is higher in primary human tumors grown as xenografts in mice that are sensitive to (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide compared to refractory tumors.
Figure 3:
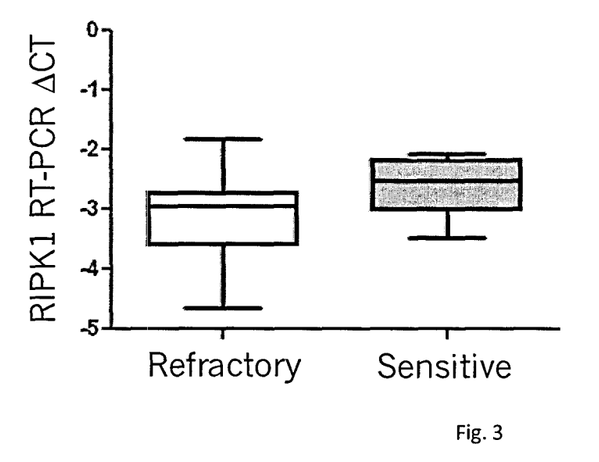
FIG. 3 shows a graph illustrating mean expression of RIPK1 mRNA measured by quantitative RT-PCR is higher in primary human tumors grown as xenografts in mice that are sensitive to (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide compared to refractory tumors.

The method for quantifying TNF, RIPK1, and STK39 mRNA by RT-PCR in primary human tumor xenografts (FIGS. 1-3) were performed as follows. RNA was extracted from primary human tumors grown in mice using the "RNeasy Mini Kit" from Qiagen (catalog number 74106). cDNA was synthesized using the "High Capacity cDNA Reverse Transcription Kit" from Applied Biosystems (part number 4368813). cDNA was pre-amplified using the "Taqman Preamp Master Mix (2×)" kit from Applied Biosystems (part number 4384266) using 50 ng of cDNA and pre-amplifying for 14 cycles. Taqman Real-Time PCR was performed in 384-well plate format with 5 microliters of pre-amplified cDNA using assays from Applied Biosystems: TNF assay ID Hs99999043_m1; RIPK1 assay ID Hs00355392_m1; STK39 assay ID Hs00202989_m1. Real-Time PCR results were normalized to 3 control genes: B2M assay ID Hs99999907_m1; HUWE1 assay ID Hs00948075_m1; UBC assay ID Hs00824723_m1.

What is claimed is:

1. A method of analyzing a biological sample of a subject with cancer, comprising determining a level of mRNA expression of biomarkers TNF and RIPK1 and one or more of the following biomarkers CXLC10, CCL5, NFKBIA, HERC5, CDYL, STK39 and MAPK14 in the biological sample taken from the subject, wherein the level of expression of the biomarkers in comparison to a control indicates that the subject has an increased likelihood of response to an Inhibitor of Apoptosis Protein (IAP) inhibitor.

2. A method of treating a subject having cancer, comprising:

assaying a biological sample from the subject for a level of expression of biomarkers TNF and RIPK1 and one or more of the following biomarkers CXLC10, CCL5, NFKBIA, HERC5, CDYL, STK39 and MAPK14 in the biological sample taken from the subject; and administering (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide to the subject on the basis that the subject's sample has been determined to have a level of biomarker expression indicative that the subject has an increased likelihood of response to (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

3. A method of treating a subject having cancer with an inhibitor of Apoptosis Protein (IAP) inhibitor, comprising administering an TAP inhibitor to the subject as a result of the subject having been determined to have a level of mRNA expression of TNF, RIPK1 and STK39 which is indicative that the subject has an increased likelihood of response to an TAP inhibitor.

4. The method according to claim 1, wherein the level of expression assayed comprises at least four biomarkers.

5. The method according to claim 1, wherein the level of expression assayed comprises at least five biomarkers.

6. The method according to claim 1, wherein the cancer is breast, ovarian or lung cancer.

7. The method according to claim 1, claim 2 or claim 3, wherein the mRNA expression level is determined using PCR, quantitative PCR or RT-PCR.

8. A kit comprising a plurality of agents for determining the level of mRNA expression of biomarkers TNF and RIPK1 and one or more of the following biomarkers CXLC10, CCL5, NFKBIA, HERC5, CDYL, STK39 and MAPK14 in a sample and instructions for use.

9. The method of claim 3, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

10. The method of claim 2, wherein the cancer is breast, ovarian or lung cancer.

11. The method of claim 3, wherein the cancer is breast, ovarian or lung cancer.

12. The method of claim 1, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

13. The method of claim 2, wherein the cancer is triple negative breast cancer.

14. The method of claim 3, wherein the cancer is triple negative breast cancer.

15. The method of claim 2, wherein the biomarkers assayed comprise TNF, RIPK1 and STK39.

16. The method of claim 1, wherein the control is a predetermined cut-off value.

17. The method of claim 2, wherein the assaying comprises generating a score from the assayed biomarker expression levels and comparing the score to a control.

18. The method of claim 3, wherein the level of mRNA expression of TNF, RIPK1 and STK39 was determined by analyzing the expression level of the biomarkers to generate a score and comparing the score to a control.

19. The method of claim 3, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

20. A method of treating a subject having cancer with an inhibitor of Apoptosis Protein (IAP) inhibitor, comprising administering an IAP inhibitor to the subject as a result of the subject having been determined to have a level of mRNA expression of biomarkers comprising TNF and RIPK1 and one or more of the following CXLC10, CCL5, NFKBIA, HERC5, CDYL, STK39 and MAPK14 in the biological sample which is indicative that the subject has an increased likelihood of response to an IAP inhibitor.

21. The method of claim 20, wherein the cancer is breast, ovarian or lung cancer.

22. The method of claim 20, wherein the cancer is triple negative breast cancer.

23. The method of claim 20, wherein the IAP inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide.

24. The method of claim 20, wherein the level of biomarker mRNA expression was determined by analyzing the expression level of the biomarkers to generate a score and comparing the score to a control.

25. The method of claim 20, where the biomarkers comprise TNF, RIPK1 and STK39.

26. The method of claim 20, wherein the mRNA expression level was determined using PCR, quantitative PCR or RT-PCR.

* * * * *